United States Patent [19]

Böhner et al.

[11] 4,076,938
[45] Feb. 28, 1978

[54] PROCESS FOR THE PRODUCTION OF 3-HYDROXY-1,2,4-TRIAZOLE DERIVATIVES

[75] Inventors: Beat Böhner, Binningen, Switzerland; Dag Dawes, Voyenenga, Norway; Willy Meyer, Riehen, Switzerland

[73] Assignee: Ciba-Geigy Corporation, Ardsley, N.Y.

[21] Appl. No.: 780,135

[22] Filed: Mar. 22, 1977

Related U.S. Application Data

[63] Continuation-in-part of Ser. No. 606,265, Aug. 20, 1975, abandoned.

[30] Foreign Application Priority Data

Aug. 29, 1974 Switzerland ................... 11771/74

[51] Int. Cl.$^2$ ............... C07D 249/12; C07D 249/14; C07D 403/04; C07D 413/04
[52] U.S. Cl. ........................ 544/132; 260/308 R; 260/308 C
[58] Field of Search ........... 260/304 B, 308 B, 308 C, 260/247.2 A, 247.5 E

[56] References Cited

U.S. PATENT DOCUMENTS

| 3,862,125 | 1/1975 | Hoffmann et al. | 260/308 R |
| 3,867,395 | 2/1975 | Seidel et al. | 260/308 R |

FOREIGN PATENT DOCUMENTS

| 2,360,631 | 6/1974 | Germany | 260/308 R |
| 307,629 | 8/1955 | Switzerland | 260/562 |
| 309,769 | 3/1956 | Switzerland | 260/562 |
| 309,770 | 11/1955 | Switzerland | 260/562 |
| 309,771 | 11/1955 | Switzerland | 260/562 |

OTHER PUBLICATIONS

Gehlen, Ann., vol. 563, pp. 185–200, (1949).

*Primary Examiner*—Alton D. Rollins
*Attorney, Agent, or Firm*—Harry Falber

[57] ABSTRACT

Process for the production of 3-hydroxy-1,2,4-triazole derivatives of the formula I

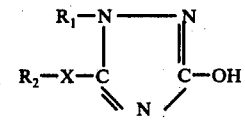

wherein $R_1$ represents an alkyl or cycloalkyl group, $R_2$ denotes an alkyl, cycloalkyl, alkenyl, alkynyl or an optionally substituted benzyl group and X stands for oxygen, sulphur or a group $<N-R_3$, wherein $R_3$ denotes an alkyl, alkenyl or alkynyl group, or together with the radical $R_2$ and the adjacent nitrogen atom it denotes a pyrrolidino or morpholino group, wherein a 2-$R_1$-hydrazinecarboxylic acid ester is reacted with cyanogen chloride to form the corresponding 2-$R_1$-2-cyanohydrazinecarboxylic acid ester which is subsequently cyclized under alkaline conditions in the presence of a compound $R_2XH$.

9 Claims, No Drawings

PROCESS FOR THE PRODUCTION OF 3-HYDROXY-1,2,4-TRIAZOLE DERIVATIVES

RELATED APPLICATION

This application is a continuation-in-part of application Ser. No. 606,265, filed Aug. 20, 1975, now abandoned.

The present invention relates to a process for the production of 3-hydroxy-1,2,4-triazole derivatives of the formula I

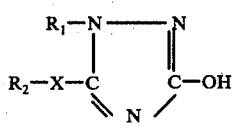

wherein
$R_1$ represents an alkyl group having 1 to 6 carbon atoms or a cycloalkyl group having 3 to 8 carbon atoms,
$R_2$ represents an alkyl group having 1 to 6 carbon atoms, a cycloalkyl group having 3 to 8 carbon atoms, an alkenyl group having 3 to 6 carbon atoms, an alkynyl group having 3 to 6 carbon atoms, or a benzyl group optionally mono- to di-substituted by alkyl having 1 to 4 carbon atoms, halogen, trifluoromethyl or nitro, and
X represents oxygen, sulphur or a group $>N-R_3$, wherein $R_3$ denotes an alkyl group having 1 to 6 carbon atoms, a alkenyl group having 3 to 6 carbon atoms, an alkynyl group having 3 to 6 carbon atoms, or together with the radical $R_2$ and the adjacent nitrogen atom it denotes a pyrrolidino or morpholino group.

The 3-hydroxy-1,2,4-triazole derivatives of the above formula I are valuable intermediates for the production of phosphoric acid esters which can be used as pestcontrol agents, especially as insecticides. Such phosphoric acid esters are described, for example, in the German 'Offenlegungsschriften' Nos. 2,259,960, 2,259,974, 2,330,089 and 2.360.687.

It is known that 1,5-disubstituted 3-hydroxy-1,2,4-triazoles of the above formula I can be produced by reaction of a semicarbazide, substituted by the radical $R_1$ according to the aforementioned definition, with orthoformic acid ester, subsequent chlorination in the 5-position of the initially resulting 3-hydroxy-1,2,4-triazole substituted in the 1-position, and replacement of the chlorine atom by the radical $R_2$-X-, wherein $R_2$ and X have the meanings given under the formula I. This known process requires a large number of reaction steps and, in addition, is unsatisfactory with regard to the attainable yields. The losses in yield occur mainly on carrying out chlorination of the 3-hydroxy-1,2,4-triazole occurring as an intermediate and on replacement of the introduced chlorine by the group $R_2X-$.

It has now been found that the 3-hydroxy-1,2,4-triazole derivative of the formula I can be produced in a simple manner by a process in which a hydrazinecarboxylic acid ester of the formula II $$R_1-NH-NH-COOR \qquad (II)$$

wherein $R_1$ has the meaning given under formula I, and R represents an alkyl radical having 1 to 4 carbon atoms, is firstly reacted with cyanogen chloride to the corresponding 2-substituted 2-cyanohydrazinecarboxylic acid ester of the formula III

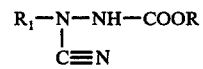

wherein $R_1$ and R have the meanings given under formulae I and II, and this is subsequently cyclised under alkaline conditions in the presence of a compound $R_2-X-H$.

The process of the invention is advantageously performed in an inert solvent. For the reaction of a hydrazinecarboxylic acid ester of the formula II with cyanogen chloride, suitable solvents are, in particular, halogenated hydrocarbons such as methylene chloride, chloroform, carbon tetrachloride, chlorobenzene, or aromatic hydrocarbons such as benzene and toluene, or ketones, especially methyl ethyl ketone, or esters, particularly ethyl acetate, or ethers and ethereal liquids such as diethyl ether, tetrahydrofuran and dioxane. For the concluding cyclisation reaction, suitable solvents are, in particular, alcohols and water, with suitable alcohols being lower alkanols having 1 to 4 carbon atoms. The cyclisation reaction can however be performed also in the absence of solvents.

The reaction of a hydrazine carboxylic acid ester of the formula II with cyanogen chloride is carried out advantageously in the presence of an acid-binding agent at a temperature of between 0 and 30° C. Suitable acid-binding agents are, in particular, alkali metal hydroxides, alkali metal carbonates and especially alkali metal hydrogen carbonates. It is furthermore advantageous to perform the reaction of a hydrazine carboxylic acid ester of the formula II with cyanogen chloride in a two-phase reaction medium consisting of water and one of the above-mentioned solvents immiscible with water.

The cyclisation reaction is performed at a temperature of between 0° and 140° C, preferably at 40° to 80° C. The reaction can be carried out at normal pressure or, if necessary, at excess pressure up to 50 atm. in an autoclave. Where the cyclisation reaction is performed in a lower alkanol, it is advantageous to operate in the presence of the corresponding sodium or potassium alcoholate. The cyclisation reaction in a lower alkanol can moreover be carried out also in the presence of sodium hydroxide or potassium hydroxide. In the case where the cyclisation reaction is performed in water, it is preferable to operate in the presence of sodium hydroxide or potassium hydroxide.

The radicals $R_1$ and $R_2$ comprise as alkyl groups straight-chain and branched-chain alkyl radicals having 1 to 6 carbon atoms. As cycloalkyl groups having 3 to 8 carbon atoms, the radicals $R_1$ and $R_2$ comprise also cycloalkyl radicals substituted in the ring by lower alkyl groups. In addition, these cycloalkyl radicals can be bound by way of 1 to 3 methylene groups to the nitrogen atom or to X. The radical $R_2$ as a benzyl group can be mono- to di-substituted in the benzene nucleus by alkyl, alkoxy, or alkylthio groups each having 1 to 4 carbon atoms, halogen, especially chlorine or bromine, nitro or trifluoromethyl.

The 2-alkyl- and 2-cycloalkylhydrazine-1-carboxylic acid esters of formula II can be prepared by reacting a hydrazine carboxylic acid ester with an aldehyde or a ketone derived from an alkyl or cycloalkyl radical represented by $R_1$ according to the above definition to obtain a corresponding hydrazone carboxylic acid ester which is subsequently hydrogenated to obtain a 2-alkyl- or 2-cycloalkylhydrazine-1-carboxylic acid ester of formula II. The preparation of 2-isopropylhydrazine-1-carboxylic acid ethyl ester, 2-cyclohexylhydrazine-1-carboxylic acid ethyl ester and 2-ethylhydrazine-1-carboxylic acid ethyl ester according to the afore-mentioned method is described in Swiss Patents 307.629, 309,669 and 309.670, respectively. Other 2-alkyl- or 2-cycloalkylhydrazine-1-carboxylic acid esters of formula II can be prepared analogously.

The process according to the invention is further illustrated by the following Examples.

EXAMPLE 1

73.0 g of 2-isopropylhydrazinecarboxylic acid ethyl ester and 42.0 g of sodium bicarbonate are stirred into 200 ml of methylene chloride and 400 ml of water. There is then introduced at room temperature in the course of 20 minutes, with continuous stirring, 30.8 g of gaseous cyanogen chloride. After an hour's stirring, the methylene chloride base is separated, dried over sodium sulphate and the solvent is distilled off in vacuo. There is obtained as residue 75.0 g (87.5% of theory) of 2-isopropyl-2-cyanohydrazinecarboxylic acid ethyl ester as colourless oil.

1370 g of 2-isopropyl-2-cyanohydrazinecarboxylic acid ethyl ester is placed into an autoclave, and 423 g of methyl mercaptan is injected. The temperature is held for 24 hours at 40° C. The resulting crystal mass is afterwards transferred to a 2.5 liter sulphonating flask, and heated in an oil bath for 2 ½ hours at 120° C. There is then added to the reaction mixture cooled to 90° C 1.2 liters of water, whereupon the the reaction product precipitates in crystalline form. Crude 1-isopropyl-5-methylthio-3-hydroxy-1,2,4-thiazole is filtered off, and recrystallised from one liter of acetonitrile. There is obtained 730 g (52% of theory) of pure 1-isopropyl-5-methylthio-3-hydroxy-1,2,4-triazole, m.p. 88°–93° C.

EXAMPLE 2

960 g of methyl mercaptan is introduced into a solution of 800 g of sodium hydroxide in 5000 ml of water, and 3024 g of 2-isopropyl-2-cyanohydrazinecarboxylic acid ethyl ester is subsequently added dropwise. During the dropwise addition, the temperature rises to 80° C and is then maintained for 2 hours at 80° C. Stirring is afterwards continued for 15 hours at 20° C. After the addition of 1200 g of glacial acetic acid, 2872 g of 1-isopropyl-5-methylthio-3-hydroxy-1,2,4-triazole, m.p. 93°–96° C, precipitates. From the filtrate there is obtained, by extraction with ethyl acetate, a further 175 g of 1-isopropyl-5-methylthio-3-hydroxy-1,2,4-triazole. The total yield is therefore 3047 g (87.5% of theory).

EXAMPLE 3

66.0 g of 2-ethylhydrazinecarboxylic acid ethyl ester and 42.0 g of sodium bicarbonate are stirred into 200 ml of methylene chloride and 400 ml of water. There is then introduced at room temperature in the course of 20 minutes, with continuous stirring, 30.8 g of gaseous cyanogen chloride. After one hour's subsequent stirring, the methylene chloride phase is separated and dried over sodium sulphate, and the solvent is distilled off in vacuo. There is obtained as residue 69.0 g (88% of theory) of 2-ethyl-2-cyano-hydrazinecarboxylic acid ethyl ester as colourless oil.

To a solution of 4.6 g of sodium in 150 ml of absolute ethanol there is added dropwise at 60° C 31.4 g of 2-ethyl-2-cyanohydrazinecarboxylic acid ethyl ester. The solution is subsequently refluxed for 4 hours. From the cooled solution there precipitates, after the addition of 12 g of glacial acetic acid, sodium acetate, which is separated by filtration. The filtrate is concentrated in vacuo to dryness, and the residue is extracted with 200 ml of chloroform. The extract is again concentrated to dryness and the residue is recrystallised from cyclohexane. There is obtained 18.8 g (60% of theory) of 1-ethyl-5-ethoxy-3-hydroxy-1,2,4-triazole, m.p. 64° to 67° C.

EXAMPLE 4

35.0 g of 2-isopropyl-2-cyanohydrazinecarboxylic acid ethyl ester is added dropwise to a solution of 100 ml of 33% dimethylamine in absolute ethanol. The solution is maintained firstly for 15 hours at room temperature and afterwards for 1 ½ hours at reflux temperature (65° C). After concentration by evaporation to dryness there remains an oily residue, which slowly crystallises on standing. The semisolid product is washed with ethyl acetate. There is obtained 15.5 g (44% of theory) of 1-isopropyl-5-dimethylamino-3-hydroxy-1,2,4-triazole, m.p. 111°–112° C.

EXAMPLE 5

48 g of methyl mercaptan is introduced into a solution of 40 g of sodium hydroxide in 300 ml of water, and 185 g of 2-sec.butyl-2-cyanohydrazinecarboxylic acid ethyl ester is subsequently added dropwise. The temperature rises to 90° C during the dropwise addition. The mixture is then allowed to cool to room temperature. After the addition of 60 g of glacial acetic acid, there precipitates 148.9 g (79.5% of theory) of 1-sec.butyl-5-methylthio-3-hydroxy-1,2,4-triazole, m.p. 104°–106° C.

The 2-sec-butyl-2-cyanohydrazinecarboxylic acid ethyl ester used as starting material is produced by methods analogous to those given in Examples 1 and 3 by reaction of 2-sec.butylhydrazinecarboxylic acid ethyl ester with cyanogen chloride.

EXAMPLE 6

905 g of methyl mercaptan is introduced into an ethanolic solution of sodium ethylate produced from 361 g of sodium and 9 liters of absolute ethanol, and an addition is subsequently made of 2470 g of 2-ethyl-2-cyanohydrazinecarboxylic acid ethyl ester. The solution obtained is kept firstly for 15 hours at room temperature and then for 3 hours at reflux temperature (80° C). After the addition of 942 g of glacial acetic acid, there precipitates from the cooled solution sodium acetate, which is separated by filtration. The filtrate is concentrated in vacuo to dryness; the residue is taken up in 7 liters of chloroform and filtration is performed. The filtrate is concentrated by evaporation at normal pressure and toluene is added; filtration is carried out and 1 liter of cyclohexane is added to the filtrate. There is obtained 1890 g (75.5% of theory) of 1-ethyl-5-methylthio-3-hydroxy-1,2,4-triazole, m.p. 83°–87° C.

EXAMPLE 7

To an ethanolic solution of sodium ethylate produced from 4.6 g of sodium and 100 ml of absolute ethanol there is firstly added dropwise 14.9 g of ethyl mercaptan and subsequently 31.4 g of 2-ethyl-2-cyanohydrazinecarboxylic acid ethyl ester is added dropwise. There is formed a crystalline precipitate, which is refluxed for 3 hours. The cooled suspension is freed, after the addition of 12 g of glacial acetic acid, by filtration from the precipitated sodium acetate, and the filtrate is concentrated in vacuo to dryness. 200 ml of chloroform is added to the residue and filtration is performed. The filtrate is again concentrated to dryness. The residue is recrystallised with cyclohexane. There is obtained 26 g (75% of theory) of 1-ethyl-5-ethylthio-3-hydroxy-1,2,4-triazole, m.p. 65°–68° C.

EXAMPLE 8

51.5 g of ethyl mercaptan and subsequently 163 g of 2-cyclopentyl-2-cyanohydrazinecarboxylic acid ethyl ester are added dropwise to a solution of 33.2 g of sodium hydroxide in 190 ml of water at room temperature. The solution is subsequently refluxed for 1 hour. From the cooled solution there precipitates, after the addition of 50 g of glacial acetic acid, 167 g (94% of theory) of 1-cyclopentyl-5-methylthio-3-hydroxy-1,2,4-triazole, m.p. 93°–95° C.

The 2-cyclopentyl-2-cyanohydrazinecarboxylic acid ethyl ester used as starting material is produced by a method analogous to that described in the Examples 1 and 3 by reaction of 2-cyclopentylhydrazinecarboxylic acid ethyl ester with cyanogen chloride.

EXAMPLE 9

244 g of allyl mercaptan is added to a solution of 132 g of sodium hydroxide in 750 ml of water, and subsequently at room temperature 514 g of 2-ethyl-2-cyanohydrazinecarboxylic acid ethyl ester is added dropwise. After one hour's refluxing, there is added to the cooled solution 198 g of glacial acetic acid. The oily phase is separated and concentrated in vacuo to dryness. There is obtained 260 g (43% of theory) of 1-ethyl-5-allylthio-3-hydroxy-1,2,4-triazole, m.p. 74°–76° C.

EXAMPLE 10

31.7 g of 4-chlorobenzyl mercaptan is added to a solution of 8 g of sodium hydroxide in 100 ml of water and 50 ml of alcohol, and subsequently 34.2 g of 2-isopropyl-2-cyanohydrazinecarboxylic acid ethyl ester is added dropwise. The temperature rises to 38° C during the dropwise addition. The temperature is then maintained for 2 hours at 85° C. After cooling of the mixture to 20° C, 12 g of glacial acetic acid is added dropwise, whereupon white crystals of 1-isopropyl-3-hydroxy-5-(4-chlorobenzylthio)-1,2,4-triazole precipitate. These are recrystallised in 400 ml of methanol and yield 42 g of product, m.p. 140°–141° C (74% of theory).

EXAMPLE 11

To a solution of 8 g of sodium hydroxide in 100 ml of water and 50 ml of alcohol there is firstly added 24.8 g of benzyl mercaptan, and subsequently 34.2 g of 2-isopropyl-2-cyanohydrazinecarboxylic acid ethyl ester is added dropwise. The temperature rises to 38° C during the dropwise addition. The temperature is then held for 2 hours at 85° C. After cooling to 20° C, there is added dropwise 12 g of glacial acetic acid, whereupon white crystals of 31 g of 1-isopropyl-3-hydroxy-5-benzylthio-1,2,4-triazole, m.p. 134°–135° C, precipitate (62% of theory).

EXAMPLE 12

24.05 g of methyl mercaptan is introduced into a solution of sodium ethylate produced by dissolving 11.5 g of sodium in 300 ml of absolute ethanol. There is then added dropwise at 60° C 71.5 g of 2-cyano-2-methylhydrazinecarboxylic acid ester, whereupon the temperature rises to 75° C. After completion of the addition, the reaction mixture is refluxed for 5 hours. 30 g of glacial acetic acid is subsequently added dropwise to the solution cooled to room temperature. After separation of the resulting precipitate by filtration, the solvent is removed in vacuo from the filtrate. With dry-ice cooling, the residue is recrystallized from 140 ml of methanol. There is obtained 21.8 g of 1-methyl-5-methylthio-3-hydroxy-1,2,4-triazole (30% of theory) having a melting point of 128°–130° C.

The 2-cyano-2-methylhydrazinecarboxylic acid ethyl ester required as starting material is produced by a method analogous to that described in Examples 1 and 3 by reaction of 2-methylhydrazinecarboxylic acid ethyl ester with cyanogen chloride.

EXAMPLE 13

26,6 g (0,15 mole) of 2-isopropyl-2-cyanohydrazinecarboxylic acid ethyl ester is added dropwise to 100 ml of pyrrolidine. The temperature raises to 30° C during the dropwise addition. The whole mixture is then stirred for 12 hours at room temperature and subsequently for 1 hour at 70° C. Then excess pyrrolidine is distilled off in vacuo. To the crystalline residue ethyl acetate is added and the crystals are filtered with suction. There is obtained 21,6 g (70% of theory) of 1-isopropyl-3-hydroxy-5-pyrrolidino-1,2,4-triazole, mp. 123°–125° C.

We claim:

1. Process for the production of 3-hydroxy-1,2,4-triazole derivatives of the formula I

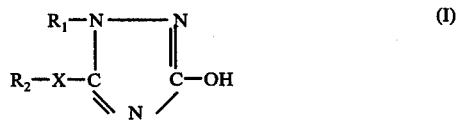

wherein

R$_1$ represents an alkyl group having 1 to 6 carbon atoms or a cycloalkyl group having 3 to 8 carbon atoms, R$_2$ represents an alkyl group having 1 to 6 carbon atoms, a cycloalkyl group having 3 to 8 carbon atoms, an alkenyl group having 3 to 6 carbon atoms, an alkynyl group having 3 to 6 carbon atoms, or a benzyl group optionally mono- to disubstituted by alkyl, alkoxy or alkylthio groups each having 1 to 4 carbon atoms, halogen, trifluoromethyl or nitro, and X represents oxygen, sulphur or a group >N—R$_3$, wherein R$_3$ denotes an alkyl group having 1 to 6 carbon atoms, an alkenyl group having 3 to 6 carbon atoms, an alkynyl group having 3 to 6 carbon atoms, or together with the radical R$_2$ and the adjacent nitrogen atom it denotes a pyrrolidino or morpholino group in which process a hydrazinecarboxylic acid ester of the formula II

wherein R$_1$ has the meaning given under formula I, and R represents an alkyl radical having 1 to 4 carbon atoms, is firstly reacted with cyanogen chloride to yield the corresponding 2-substituted 2-cyanohydrazinecarboxylic acid ester of the formula III

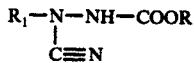

wherein $R_1$ and R have the meanings given under the formulae I and II, and the resulting intermediate product is subsequently cyclised under alkaline conditions in the presence of a compound $R_2XH$.

2. Process according to claim 1, wherein the reaction of the hydrazinecarboxylic acid ester of the formula II with cyanogen chloride is performed at a temperature of between 0° and 30° C in an inert solvent in the presence of an acid-binding agent.

3. Process according to claim 1 wherein the reaction of a hydrazinecarboxylic acid ester of the formula II with cyanogen chloride is performed in a two-phase reaction medium consisting of water and a solvent immiscible with water.

4. Process according to claim 1 wherein the cyclisation reaction is performed at a temperature between 0° and 140° C.

5. Process according to claim 1 wherein the cyclisation reaction is performed at a temperature between 40° and 120° C.

6. Process according to claim 1 wherein the cyclisation reaction is performed in a lower alkanol.

7. Process according to claim 1 wherein the cyclisation reaction is performed in water.

8. Process according to claim 1 wherein the cyclisation reaction is performed in a lower alkanol in the presence of the corresponding sodium or potassium alcoholate.

9. Process according to claim 1 wherein the cyclisation reaction is performed in water in the presence of sodium hydroxide or potassium hydroxide.

* * * * *